United States Patent [19]

Travis

[11] Patent Number: 4,605,616

[45] Date of Patent: * Aug. 12, 1986

[54] DETERMINATION OF OXIDIZED α-1-PROTEINASE INHIBITOR IN SERUM OR PLASMA

[75] Inventor: James Travis, Athens, Ga.

[73] Assignee: University of Georgia Research Foundation, Inc., Athens, Ga.

[*] Notice: The portion of the term of this patent subsequent to Jan. 15, 2001 has been disclaimed.

[21] Appl. No.: 654,966

[22] Filed: Sep. 27, 1984

Related U.S. Application Data

[63] Continuation of Ser. No. 402,442, Jul. 27, 1982, Pat. No. 4,493,891.

[51] Int. Cl.$^4$ .......................... C12Q 1/38; C12N 9/99
[52] U.S. Cl. ...................................... 435/23; 435/184
[58] Field of Search .......................... 435/4, 7, 23, 184

[56] References Cited

PUBLICATIONS

Beatty et al., Chemical Abstracts, 97: 121454n, 168–169 (1982).

Abrams et al., Proc. Nat'l. Acad. Sci. USA, 78(12): 7483–7486 (1981).

Carp et al., Proc. Nat'l. Acad. Sci. USA, 79: 2041–2045 (Mar. 1982).

Turins et al., Science, 165: 709–710 (1969).

Travis et al., *Methods in Enzymology*, 80, Academic Press, New York, 754–765 (1981).

*Primary Examiner*—Esther M. Kepplinger
*Attorney, Agent, or Firm*—Oblon, Fisher, Spivak, McClelland & Maier

[57] ABSTRACT

A new method of determining oxidized α-1-proteinase inhibitor in serum or plasma for use in studying the development of chronic obstructive lung disease is disclosed. Levels of oxidized α-1-proteinase inhibitor indicate the potential for emphysema development with higher levels showing a decrease in lung protection against elastolytic enzymes such as elastase. This method can be used for patients with a potential for chronic obstructive lung disease rather than having to use bronchial lavage methods for such patients. No other method is known to exist for determining oxidized α-1-proteinase inhibitor in serum or plasma.

2 Claims, 2 Drawing Figures

DETERMINATION OF OXIDIZED α-1-PROTEINASE INHIBITOR IN SERUM OR PLASMA

The Government has rights in this invention pursuant to grant No. HL26148 awarded by the Department of Health and Human Services.

This is a continuation of application Ser. No. 402,442, filed July 27, 1982, now U.S. Pat. No. 4,493,891.

BACKGROUND AND SUMMARY OF THE INVENTION

This invention relates to a method of determining oxidized α-1-proteinase inhibitor in serum or plasma. This method is a diagnostic technique useful in studying the development of chronic obstructive lung disease. More specifically this method is useful for patients having a potential for chronic obstructive lung disease rather than using bronchial lavage methods. No other method is known to exist for determining oxidized α-1-proteinase inhibitor in serum or plasma.

Pulmonary emphysema appears to be a consequence of accelerated lung elastin degradation that results from either an elevated level of elastase activity or a decreased level of elastase inhibitor(s) within the lung, or a combination of both factors. Neutrophil elastase is probably the major elastolytic activity involved in development of emphysema although elastase activity from other sources such as macrophages and monocytes may have a role. The principal inhibitor of neutrophil elastase is the plasma protein α-1-proteinase inhibitor (formerly referred to as α-1-antitrypsin). Severe genetic deficiencies of this protein commonly result in emphysema in the affected individuals. α-1-proteinase prevents the accumulation of leukocytes which contain proteases such as elastase within their cytoplasmic granules.

Most smokers who develop emphysema do so despite normal levels of α-1-proteinase inhibitor. An explanation for emphysema in smokers with normal α-1-proteinase inhibitor concentrations has evolved from the observation of the ease of oxidation of the reactive site methionyl residue of this protein leading to a two-thousand fold reduced rate of association of the oxidized inhibitor with human leukocyte elastase. Thus, reduced levels of elastase inhibitory activity can result from partial oxidation of the α-1-proteinase inhibitor in the lung through inhalation of oxidants present in tobacco smoke, ozone, or industrial gases, as well as from oxidants released from cells in the lung, even if levels of plasma α-1-proteinase inhibitor are normal or elevated.

Chronic obstructive lung disease has been associated with α-1-antitrypsin (now referred to as α-1-proteinase inhibitor) deficiency wherein extraordinarily low levels of elastase inhibition were found in the serum of the survey patients, assaying α-1-antitrypsin activity by a standard assay known in the art (Turino, G. M., Senior, R. M., Bhagwin, D. C., Keller, S., Levi, M. M., and Mandl, I., *Science,* 165:709, 1969). Release of proteolytic enzymes in lungs and the onset of emphysema have been linked to cigarette smoking (Hutchinson, D. C. S., *Brit. J. Dis. Chest.* 67:171, 1973). The relationship of leukocytic proteases to lung tissue degradation and α-1-antitrypsin inhibitor (now referred to as α-1-proteinase inhibitor) deficiency has been described which showed a correlation between serum leukocytic elastase inhibitory capacity and serum trypsin inhibitory capacity wherein both trypsin and elastase were inhibited by α-1-antitrypsin (Lieberman, J., *Arch. Environ. Health* 27:196, 1973). The proteolytic enzyme elastase has been reported to cause irreversible lung damage after laboratory animals received intratrachial injections of pancreatic porcine elastase (Kaplan, P. D., Kuhn, C., and Pierce, J. A., *J. Lab. Clin. Med.* 82:349, 1973). The Eriksson (Laurell, C. B. and Eriksson, S., *Scand. J. Clin. Lab. Invest.* 15:132-134, 1963) method of emphysema diagnosis has been analyzed and an attempt has been made to determine the probability of the occurrence of phenotypes predisposed to emphysema when low α-1-antitrypsin (now referred to as α-1-proteinase inhibitor) values were found using gelatinous film or immunochemical methods (Pilacik, B. and Kowalczyk, J., *Med. Pr.* 30(3):207, 1979). The oxidant effect of cigarette smoking has been reported wherein several mechanisms have been suggested by which tobacco smoke damages the lungs (Kimbel, P. and Kueppers, F., *Ann. Intern. Med.* 92(4):564, 1980). The concentration of proteases and antiproteases of the lower respiratory tract in normal individuals have been compared with those who smoke or have deficiency of serum α-1-antitrypsin (now referred to as α-1-proteinase inhibitor) wherein a mechanism of elastase production within the the alveoli of the lung has been suggested (Gadek, J. E., Hunninghake, G. W., Fells, G. A., Zimmerman, R. L., Keogh, B. A., and Crystal, R. G., *Bull. europ. Physiopath. resp.* 16 (Suppl.):27, 1980). Cigarette smoke has been described as an oxidant of α-1-proteinase inhibitor wherein as little as three puffs of cigarette smoke caused a significant decrease in the elastase inhibitor capacity per milligram of α-1-proteinase inhibitor (Janoff, A., Carp, H., and Lee, D. K., *Bull. europ. Physiopath.* 16 (Suppl.):321, 1980). A cycle has been proposed wherein proteolytic enzymes not only degrade tissue abnormally but also increase the production of oxidants to turn off inhibitor control of proteinases resulting in predicted rapid changes in proteinase levels and proteinase inhibitor levels (Travis, J., Beatty, K., Wong, P. S., and Matheson, N. R., *Bull. europ. Physiopath resp.* 16 (Suppl.):341, 1980). A gel plate assay for the detection of elastase activity and for the meaurement of serum elastase inhibitory capacity has been reported which provides an indirect means for estimating α-1-antitrypsin (now referred to as α-1-proteinase inhibitor) function (Billingsly, G. D. and Cox, D. W., *Am. Rev. resp. Disease.* 121 (1):161-164, 1980).

The present invention described a convenient method for determining the percent of normal versus oxidized α-1-proteinase inhibitor in human serum or plasma based on a measurable difference between the inhibitory activities of normal and oxidized α-1-proteinase inhibitor against a trypsin like enzyme and elastase. It is an object of the present invention to provide a method of determining oxidized α-1-proteinase inhibitor in serum or plasma.

It is an object of the present invention to provide a method for determining the quantity of normal versus oxidized α-1-proteinase inhibitor against a trypsin like enzyme and elastase.

It is an object of the present invention to provide a useful diagnostic technique in studying the development of chronic obstructive lung disease.

It is a further object to provide a useful diagnostic technique in studying patients having a potential for chronic obstructive lung disease rather than using bronchial lavage methods.

These and other objects, aspects, and advantages of this invention will become apparent from a consideration of the accompanying specification and claims.

BRIEF DESCRIPTION OF THE DRAWINGS

FIG. 2 shows the effect of α-2-macroglobulin (α-2M) on the relative trypsin like inhibitory capacity (TIC)/elastase inhibitory capacity (EIC) of a α-1-proteinase inhibitor (α-1PI). The ordinate is the relative trypsin like inhibitory capacity(TIC)/elastase inhibitory capacity (EIC) of different concentrations of oxidized α-1-proteinase inhibitor (α-1PI) (1.3 mg/ml) in the presence of α-2-macroglobulin (α-2M) (2 mg/ml). The abscissa is the relative trypsin like inhibitory capacity (TIC)/elastase inhibitory capacity (EIC) of partially oxidized preparations of α-1-proteinase inhibitor (α-1PI) (1 m/gml) in the absence of α-2-macroglobulin (α-2M).

GENERAL DESCRIPTION OF THE INVENTION

Figure 1:
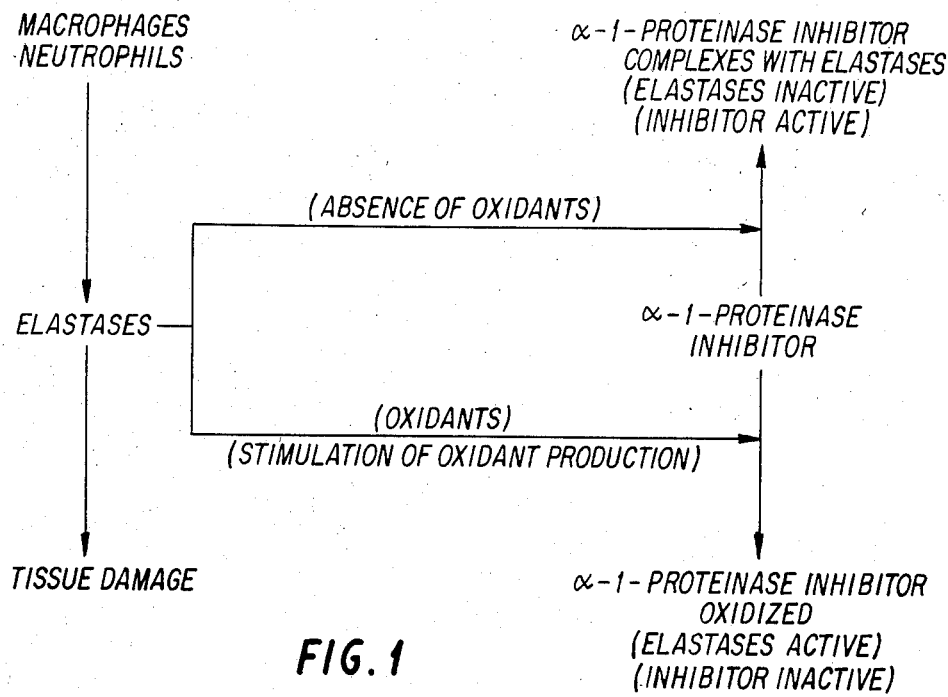
FIG. 1 shows interactions among macrophages, neutrophils, proteinases, and oxidants in the inactivation of α-1-proteinase inhibitors and the development of tissue damage. Elastases, which are a major type of proteinases from macrophages and neutrophils, are normally inactivated by α-1-proteinase inhibitor. In the absence of oxidants, α-1-proteinase inhibitor is actived and complexes with elastases wherein the elastases are inactivated. Elastases increase the production of oxidants. In the presence of oxidants, α-1-proteinase inhibitor is oxidized. Oxidized α-1-proteinase inhibitor is an inactive inhibitor. In the absence of active α-1-proteinase inhibitor, elastases degrade tissue abnormally causing tissue damage.

Levels of oxidized α-1 proteinase inhibitor indicate the potential for emphysema development with higher levels showing a decrease in lung protection against elastolytic enzymes such as elastase.

"Trypsin like enzyme" is a term used to describe any enzyme which inhibits α-1-proteinase inhibitor. Trypsin like enzymes include but are not limited to the following enzymes: trypsin, chymotrypsin, thrombin, plasmin, cathepsin C, and acrosin.

An unknown sample of serum or plasma contains α-1-proteinase inhibitor as a component of the serum or plasma. Similarly, a standard reduced sample of serum or plasma contain α-1-proteinase inhibitor as a component of the serum or plasma.

A standard solution of a trypsin like enzyme refers to a solution containing a known amount of trypsin like enzyme. Similarly, a standard solution of an elastase refers to a solution containing a known amount of elastase.

The method for this invention for determining percent of oxidized α-1-proteinase inhibitor, X, present in an unknown sample of serum or plasma comprises:

(a) assaying a portion of the unknown sample of serum or plasma for enzymatic activity of a trypsin like enzyme;

(b) assaying a portion of the unknown sample of serum or plasma for enzymatic activity of an elastase;

(c) selecting known standards and determining their activity for both the trypsin like enzyme and elastase;

(d) determining an oxidized ratio, $K_o$, of the unknown sample of serum or plasma wherein $$K_o = \frac{\text{trypsin like inhibitory capacity}}{\text{elastase inhibitory capacity}} = \frac{T_k - T_u}{E_k - E_u}$$

wherein $T_k$=Enzymatic activity of the trypsin like enzyme in a standard solution of the trypsin like enzyme;

wherein $T_u$=Enzymatic activity of the trypsin like enzyme of an unknown solution comprising the standard solution of the trypsin like enzyme and the unknown sample of serum or plasma;

wherein $E_k$=Enzymatic activity of the elastase in a standard solution of the elastase; and wherein $E_u$=Enzymatic activity of the elastase of an unknown solution comprising the standard solution of the elastase and the unknown sample of serum or plasma;

(e) determining a reduced ratio, $K_R$, of a standard reduced sample of serum or plasma, wherein $$K_R = \frac{\text{trypsin like inhibitory capacity}}{\text{elastase inhibitory capacity}} = \frac{T_k - T_r}{E_k - E_r}$$

wherein $T_k$=Enzymatic activity of a trypsin like enzyme in a standard solution of the trypsin like enzyme;

wherein $T_r$=Enzymatic activity of the trypsin like enzyme of a known solution comprising the standard solution of the trypsin like enzyme and the standard reduced sample of serum or plasma;

wherein $E_k$=Enzymatic activity of an elastase in a standard solution of the elastase; and wherein $E_r$=Enzymatic activity of the elastase of a known solution comprising the standard solution of the elastase and the standard reduced sample of serum or plasma;

(f) substituting the reduced ratio and the oxidized ratio into an equation $$X = \left(1 - \frac{K_R}{K_o}\right) 100$$

and solving the equation for X, the percent of oxidized α-1-proteinase inhibitor.

Since sensitivity of measuring enzymatic activity of trypsin like enzymes has been found to be relatively affected by actual enzyme concentrations used, standards are selected that approximate the sample. More specifically, trypsin like enzyme concentrations are selected which approximate the unknown sample of serum or plasma. Similarly, since sensitivity of measuring enzymatic activity of elastases has been found to be relatively affected by actual enzyme concentrations used, standards are selected that approximate the sample. More specifically, elastase enzyme concentrations are selected which approximate the unknown sample of serum or plasma.

DETAILED DESCRIPTION OF THE INVENTION

The following description more particularly sets forth a method for determining percent of oxidized α-1-proteinase inhibitor present in an unknown sample based on a measurable difference between the inhibitory activities of normal and oxidized α-1-proteinase inhibitor against a trypsin like enzyme and elastase. Normal α-1-proteinase inhibitor inhibited porcine trypsin and porcine pancreatic elastase. Oxidized α-1-proteinase inhibitor lost its inhibitory activity towards porcine pancreatic elastase while its net porcine trypsin inhibitor capacity (trypsin like inhibitory capacity) was retained, although the rate of association with trypsin was markedly reduced. Thus, the reduced ratio, $K_R$, of a standard reduced sample of serum or plasma (net porcine trypsin inhibitory capacity to net porcine elastase inhibitory capacity) of fully reduced α-1-proteinase inhibitor was a constant wherein its value depended solely upon the assays used and the units of measurement as shown in equation (1), below.

$$\frac{\text{trypsin like inhibitory capacity}}{\text{elastase inhibitory capacity}} = K_R \quad (1)$$

Trypsin like inhibitory capacity refers to a capacity to be inhibited by α-1-proteinase inhibitor. As α-1-proteinase inhibitor was progressively oxidized this ratio changed to a higher value $K_o$, an oxidized ratio of an unknown sample of serum or plasma in proportion to the fractional loss of elastase inhibitory capacity represented as X, which also equals the fractional oxidation of α-1-proteinase inhibitor as shown in equation (2a) below.

$$\frac{\text{trypsin like inhibitory capacity}}{\text{elastase inhibitory capacity}} = K_o \quad (2a)$$

For an unknown sample $K_o$ is determined as shown in equation (2b) below.

$$K_o = \frac{\text{trypsin inhibitory capacity}}{\text{elastase inhibitory capacity}} \quad (2b)$$

The more oxidized the α-1-proteinase inhibitor the higher the ratio of trypsin like inhibitory capacity/elastase inhibitory capacity became until the ratio approached infinity for completely oxidized α-1-proteinase inhibitor. Substituting $K_R$ from equation 1 into equation 2 gave equation (3) below.

$$\frac{K_R}{1-X} = K_o \quad (3)$$

If the ratio $K_R$ was known from a standard reduced sample of serum or plasma, and the ratio $K_o$ of an unknown sample of serum or plasma was measured, the fraction of oxidized α-1-proteinase inhibitor in the unknown can be calculated from a rearrangement of equation (3), above resulting in equation (4) below.

$$X = 1 - \frac{K_R}{K_o} \quad (4)$$

The percent of oxidized α-1-proteinase inhibitor, X, can be determined by multiplying by 100 as shown in equation (5), below, and solving for X, the percent of oxidized α-1-proteinase inhibitor.

$$X = \left(1 - \frac{K_R}{K_o}\right) 100 \quad (5)$$

METHODS

Venous blood was collected from healthy young volunteers, according to a protocol approved by the Human Studies Committee of the Jewish Hospital of St. Louis, St. Louis, Mo. The blood was allowed to clot overnight at 4° C. and the serum removed by centrifugation. Ten of the twenty samples collected were from individuals who regularly smoked one to two packs of cigarettes per day. All of the smokers had been smoking within several hours of blood collection.

N-chlorosuccinimide was obtained from the Aldrich Chemical Co. Benzoyl-L-Arginine ethyl ester was a product of Worthington Biochemicals Corp. and was usually stored frozen as a stock solution of 30 mg/ml in 90% acetonitrile, 10% dimethyl sulfoxide. Succinyl-L-alanyl-alanyl-alanyl-paranitroanilide was purchased from BACHEM, Inc. and was stored as a 0.2M stock solution in dimethyl sulfoxide.

Porcine trypsin and porcine pancreatic elastase (Sigma Chemical Corp.) were prepared as stock solutions of 5 mg/ml in $10^{-3}$M HCl and 0.05M Tris, 0.05M NaCl, pH 8.0, respectively. Both solutions were stored frozen. Human α-1-proteinase inhibitor and human α-2-macroglobulin were prepared using methods of Pannell, R., Johnson, D., and Travis, J., Biochemistry 13:5439, 1974 and of Virca, G. D., Travis, J., Hall, P. K., and Roberts, R. C., Anal. Biochem. 89:274, 1978 which are known in the art. Oxidized α-1-proteinase inhibitor was prepared by the addition of eight molar equivalents of N-chlorosuccinimide to the native protein at pH 9.0, followed by exhaustive dialysis against 0.05M Tris-HCl, 0.05M NaCl, pH 8.0 (7). Reduction of the oxidized protein was performed by the method of Jori, G., Galiazzo, G., Marzotto, A., and Scoffone, E., J. Biol. Chem. 243:4272, 1968 which is known in the art using a 5% solution of 2-mercaptoethanol, incubated with the protein for four days at pH 8.0 and 23° C. The half time for reduction was one day. The reduced α-1-proteinase inhibitor was exhaustively dialyzed against 0.05M Tris-HCl, 0.05M NaCl, pH 8.0, in a stoppered flask through which nitrogen was bubbled to remove oxygen and was referred to as an example of a standard reduced sample of serum or plasma.

EXAMPLE I

Assay for Porcine Trypsin Activity

Five microliters of stock trypsin solution was mixed with 100 μl of 0.2M Tris-HCl, pH 8.0, in a 3.0 ml cuvette. The volume was adjusted to 3.0 ml by addition of 0.05M TrisHCl, pH 8.0 and 20 μl of stock N-benzoyl-L-arginine ethyl ester as a substrate was then added (standard solution of trypsin like enzyme). Trypsin activity was measured as the change in absorbance at 253 nanometers per minute ($\Delta A_{253}$/min) using the method of Schwert, G. W., and Takenaka, Y., Biochim. Biophys. Acta. 16:570, 1955 which is known in the art.

EXAMPLE II

Assay for Porcine Pancreatic Elastase Activity

Five microliters of stock elastase solution was mixed with 100 μl of 0.2M Tris-HCl, pH 8.0, in a 3.0 ml cuvette. The volume was adjusted to 3.0 ml by addition of 0.05M Tris-HCl, pH 8.0, and 20 μl of stock Succinyl-L-alanyl-L-alanyl-L-alanyl-paranitroanilide as a substrate was then added (standard solution of elastase). Elastase activity was measured as the change in absorbance at 400 nanometers per minute ($\Delta A_{400}$/min) using the method of Bieth, J., Speiss, B., and Wermuth, C. G., Biochem. Med. 11:353, 1974 which is known in the art.

EXAMPLE III

Assay of Inhibitory Activity of α-1-proteinase Inhibitor

Twenty microliters of α-1-proteinase inhibitor or serum were mixed with 100 μl of 0.2M Tris-HCl, pH 8.0, in a 3.0 ml cuvette. Five microliters of stock trypsin or porcine pancreatic elastase were then added. After the mixture had incubated ten minutes, the volume was brought to 3.0 ml with 0.05M Tris-HCl, pH 8.0, and 20 μl of either stock trypsin substrate or stock elastase substrate was added. Residual enzyme activity was then measured as described above. Inhibitory activities for trypsin like enzyme (trypsin like inhibitor capacity) and elastase (elastase inhibitor capacity) were calculated by measuring activity differences between a standard enzyme solution alone and the same solution to which α-1-proteinase inhibitor had been added as shown in equations (6a) and (6b), below.

$$\text{trypsin like inhibitor capacity} = (\Delta A_{253}/\text{min})_{trypsin\,like\,enzyme} - \quad (6a)$$

$$(\Delta A_{253}/\text{min})_{trypsin\,like\,enzyme\,+\,\alpha\text{-1-proteinase inhibitor}}$$

$$\text{elastase inhibitor capacity} = (\Delta A_{400}/\text{min})_{elastase} - \quad (6b)$$

$$(\Delta A_{400}/\text{min})_{elastase\,+\,\alpha\text{-1-proteinase inhibitor}}$$

For an unknown sample of serum or plasma, trypsin inhibitor capacity and elastase inhibitor capacity were determined as shown in equations (6a) and (6b), above, wherein the unknown sample of serum or plasma contained the α-1-proteinase inhibitor. For a standard reduced sample of serum or plasma, prepared as described in Methods, above, trypsin like inhibitor capacity and elastase inhibitor capacity were determined as shown in equations (6a) and (6b), above, wherein the standard reduced sample of serum or plasma contained the α-1-proteinase inhibitor.

Inactivation of α-1-proteinase inhibitor by the oxidizing agent N-chlorosuccinimide increased the trypsin like inhibitory capacity/elastase inhibitory capacity ratio as shown in Table 1, below, for purified, mercaptoethanol-reduced α-1-proteinase inhibitor from 1.27 to 130. The effect showed the utility of the assay in detecting oxidized α-1-proteinase inhibitor in tissue samples. Substitution of the values 1.27 for $K_R$ and 130 for $K_o$ in equation (4), above, gives the result that 99% of the α-1-proteinase inhibitor was oxidized by N-chlorosuccinimide. The percent approached 100% which indicated the ratio approached infinity.

When the trypsin like inhibitory capacity/elastase inhibitory capacity ratios were compared in the serum samples of smokers and non-smokers significant differences, (P=0.005), were noted, see Tables 1 and 2, below.

TABLE 1

Inhibitory Activity Ratios of Native α-1-proteinase inhibitor and Human Serum from Non-Smokers and Smokers.

| | trypsin like inhibitory capacity / elastase inhibitory capacity | percent of oxidized α-1-proteinase inhibitor (α-1PI) = $\left(1 - \frac{1.27}{K_o}\right) 100$ |
|---|---|---|
| α-1-PI (native, reduced) | 1.27 | 0 |
| α-1-PI (native, oxidized) | 130 | 99 |
| Serum (10 non-smokers) | 1.25 | 0 |
| Serum (10 smokers) | 1.60 | 23 |

TABLE 2

Inhibitory Activity Ratios of Serum from Non-Smokers and Smokers trypsin like inhibitory capacity / elastase inhibitory capacity

| | Non-Smokers | Smokers |
|---|---|---|
| | 1.25 | 1.66 |
| | 1.24 | 1.48 |
| | 1.22 | 1.50 |
| | 1.11 | 1.26 |
| | 1.30 | 1.71 |
| | 1.14 | 1.81 |
| | 1.32 | 1.74 |
| | 1.14 | 1.53 |
| | 1.27 | 1.54 |
| | 1.44 | 1.63 |
| Average | 1.25 | 1.60 |
| Std. Deviation | 0.11 | 0.17 |

In the samples from non-smokers the average trypsin like inhibitory capacity/elastase inhibitory capacity ratio, 1.25, matched the ratio of 1.17 found for purified, mercaptoethanol-reduced α-1-proteinase inhibitor indicating that α-1-proteinase inhibitor of non-smokers is in a chemically reduced state. Smokers' serum, however, contained oxidized α-1-proteinase inhibitor, reflected by an average trypsin inhibitory like capacity/elastase inhibitory capacity ratio of 1.60. Substituting 1.60 for $K_o$ and 1.25 for $K_R$ in equation (5), above, leads to the result that 23% of the α-1-proteinase inhibitor in smokers was oxidized. One non-smoker had a high ratio and one smoker had a low ratio. The specific reasons why these two individuals are exceptional are not yet known but likely reflect other genetic patterns which influence the rate at which α-1-proteinase inhibitor is oxidized.

Measurement of the total α-1-proteinase inhibitor by immunoelectrophoresis indicated that the average values of the serum from smokers was about 143% of normal, relative to a standard pool with the non-smokers at the normal value. The findings of elevated α-1-proteinase inhibitor in smokers is in agreement with results published elsewhere.

The present invention offers several advantages in that (a) a ratio is inherently more sensitive than measurements based on a single observation; (b) the results are not influenced by the concentration of α-1-proteinase inhibitor, nor by partial denaturation of α-1-proteinase inhibitor, nor by the purity of the α-1-proteinase inhibitor; (c) the assays refer directly to a standard reduced sample of serum or plasma containing the α-1-proteinase inhibitor which is easily prepared; (d) any trypsin like enzyme such as porcine trypsin or bovine α-chymotrypsin and any known assay therefor are used; (e) similarly, any elastase and any known assay therefor are used; (f) the results convert directly to percent oxidation of α-1-proteinase inhibitor, and the data given in Tables 1 and 2, above, show that the assay is useful over a broad range and sensitive enough to identify the effects of smoking on α-1-proteinase inhibitor.

Although the loss of elastase inhibitory capacity without a corresponding loss of trypsin like inhibitory capacity is typical of oxidation of α-1-proteinase inhibitor, non-oxidizing regents can also effect a disproportionate loss of porcine elastase inhibitory capacity of human α-1-proteinase inhibitor and thus could interfere with the interpretation of results obtained with this assay. For example, there was a 70% loss of elastase inhibitory capacity with only a 30% loss of trypsin inhibitory capacity after a twenty four hour incubation of human α-1-proteinase inhibitor at pH 8.0, 37° C., in a 15 mM solution of the methylating agent, methyl iodide. Similarly, chemical modification of the tyrosyl residues of α-1-proteinase inhibitor with tetranitromethane or N-acetylimidazole have been reported to result in a selective loss of elatase inhibitory capacity and iodination has the same effect. Using the methods of the present invention, 23% of the α-1-proteinase inhibitor in serum of smokers appears to be in the oxidized form. This value is in agreement with a published report that smokers' serum elastase inhibitory capacity was 20% less than expected of the immunologically determined titer of serum α-1-proteinase inhibitor. The present invention provides a method which is useful in studying the development of chronic obstructive lung disease such as emphysema. This method is useful in predicting the occurrence of chronic obstructive lung disease such as emphysema in persons having a potential for chronic obstructive lung disease such as smokers.

The oxidation of α-1-proteinase inhibitor totally eliminates its inhibitory activity for porcine elastase, while only significantly affecting its behavior toward trypsin like enzymes.

Porcine enzymes were used because human enzymes are not available; however, human enzymes, if available commercially, could be substituted for porcine enzymes with the same or better results.

EXAMPLE IV

Effect of α-2-Macroglobulin

Figure 2:
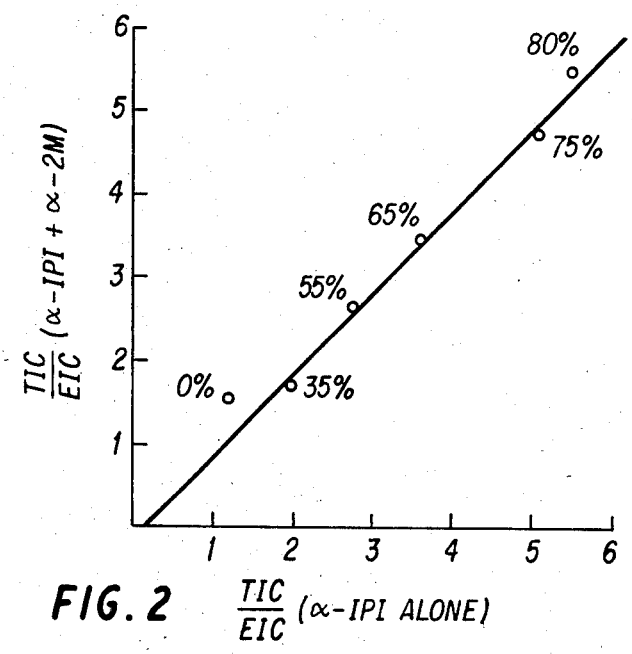
FIG. 2 is provided to show that α-2-macroglobulin, another major serum proteinase inhibitor which is known to inactivate proteolytic activity of serine proteinases without affecting esterolytic activity, does not affect the method of this invention for measuring oxidized α-1-proteinase inhibitor.

Since α-2-macroglobulin can inactivate the proteolytic activity of serine proteinases without affecting esterolytic activity, the possible interfering effect of this inhibitor in the assays described above was investigated. Samples of α-1-proteinase inhibitor at several different degrees of oxidation were made by mixing different proportions of completely oxidized α-1-proteinase inhibitor with reduced α-1-proteinase inhibitor. Each solution of partially oxidized inhibitor was diluted to 1.3 mg/ml with buffer alone and to 1.3 mg/ml in the presence of 2 mg/ml of α-2-macroglobulin. At a concentration of 2 mg/ml the α-2-macroglobulin inhibited an equal volume of $1.0 \times 10^{-6}$M active porcine trypsin. The concentrations of α-1-proteinase inhibitor and α-2-macroglobulin were chosen to approximate their concentration in whole plasma. Both α-1-proteinase inhibitor alone, as well as α-1-proteinase inhibitor mixed with 2 mg/ml of α-2-macroglobulin, were assayed for trypsin like inhibitory capacity and elastase inhibitory capacity. The trypsin like inhibitory capacity/elastase inhibitory capacity ratios were then compared to determine if they were the same with and without the added α-2-macroglobulin.

α-2-macroglobulin had no effect on the procedures described for measuring oxidized -1-proteinase inhibitor levels. As shown in FIG. 2, there was no change in the trypsin like inhibitory capacity/elastase inhibitory capacity ratio irrespective of the presence of α-2-macroglobulin. Such a result can only be interpreted as meaning that α-2-macroglobulin does not interfere in the assays. The data in this figure also depict the trypsin like inhibitory/elastase inhibitory capacity ratios for varying percentages of oxidized α-1-proteinase inhibitor.

EXAMPLE V

Other Proteins in Plasma

In order to determine whether other proteins in plasma might interfere with the trypsin inhibitory capacity and elastase inhibitory capacity assays, experiments were performed in which samples of α-1-proteinase inhibitor at several different degrees of oxidation were incubated with serum containing low levels of α-1-proteinase inhibitor in the concentration of this inhibitor being less than 10% of normal. Assays for trypsin like inhibitory capacity and elastase inhibitory capacity were then performed to determine if the addition of the partially oxidized inhibitor to this serum had any effect on the trypsin line inhibitory capacity and elastase inhibitory capacity ratio.

Similarly, the effect of other plasma proteins on the trypsin like inhibitory capacity and elastase inhibitory capacity assays was found to be essentially negative. Again, the trypsin like inhibitory capacity/elastase inhibitory capacity ratios did not change for various partially oxidized α-1-proteinase inhibitor samples when added to α-1-proteinase inhibitor deficient plasma and a pattern similar to that shown in FIG. 2 was obtained.

The foregoing illustrates specific embodiments within the scope of this invention and is not to be construed as limiting said scope. It is to be understood that variations and modifications thereof may be made by those skilled in the art without departing from the scope of the invention.

What is claimed is:

1. A method for determining the presence of oxidized α-1-proteinase inhibitor in an unknown sample of serum or plasma, which comprises:
   (a) determining the reduction in activity of an enzyme inhibitable by α-1-proteinase inhibitor in the presence of a first portion of said sample;
   (b) determining the reduction in activity of an elastase enzyme in the presence of a second portion of said sample; and
   (c) comparing the relative amount of reduction of activity in steps (a) and (b) to the relative amount of reduction in activity of said enzyme inhibitable by α-1-proteinase inhibitor and said elastase enzyme in the presence of a reduced standard sample of α-1-proteinase inhibitor, wherein the same relative reduction in activity indicates reduced α-1-proteinase inhibitor and a lesser relative reduction in activity of elastase enzyme compared to activity of said enzyme inhibitable by α-1-proteinase inhibitor indicates the presence of oxidized α-1-proteinase inhibitor.

2. The method of claim 1 wherein said enzyme inhibitable by α-1-proteinase inhibitor is trypsin.

* * * * *